US011844889B2

(12) United States Patent
Irrgang

(10) Patent No.: US 11,844,889 B2
(45) Date of Patent: Dec. 19, 2023

(54) EXTRACORPOREAL BLOOD TREATMENT DEVICE AND METHOD FOR OPERATING AN EXTRACORPOREAL BLOOD TREATMENT DEVICE

(71) Applicant: FRESENIUS MEDICAL CARE DEUTSCHLAND GMBH, Bad Homburg (DE)

(72) Inventor: Tobias Irrgang, Aubstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 17/989,882

(22) Filed: Nov. 18, 2022

(65) Prior Publication Data

US 2023/0079237 A1 Mar. 16, 2023

Related U.S. Application Data

(62) Division of application No. 16/487,103, filed as application No. PCT/EP2018/054197 on Feb. 21, 2018, now Pat. No. 11,529,446.

(30) Foreign Application Priority Data

Feb. 23, 2017 (DE) ..................... 10 2017 001 770.0

(51) Int. Cl.
*A61M 1/16* (2006.01)
*A61M 39/22* (2006.01)

(52) U.S. Cl.
CPC .......... *A61M 1/1686* (2013.01); *A61M 1/165* (2014.02); *A61M 1/1657* (2022.05);
(Continued)

(58) Field of Classification Search
CPC ................ A61M 1/165; A61M 1/1686; A61M 2205/33; A61M 2205/75; A61M 39/223
See application file for complete search history.

(56) References Cited

U.S. PATENT DOCUMENTS 4,695,385 A 9/1987 Boag
4,728,496 A 3/1988 Peterson et al.
(Continued)

FOREIGN PATENT DOCUMENTS

DE 69533446 T2 1/2005
DE 102014106490 A1 11/2015
(Continued)

OTHER PUBLICATIONS

International Search Report and Written Opinion issued in corresponding International Patent Application No. PCT/EP2018/054197 (with English translation of International Search Report) dated May 15, 2018 (13 pages).
(Continued)

*Primary Examiner* — Dirk R Bass
(74) *Attorney, Agent, or Firm* — Kilyk & Bowersox, P.L.L.C.

(57) ABSTRACT

An extracorporeal blood treatment device is provided that includes a hydraulic system having a plurality of flow paths. A control unit provides an operating mode for disinfecting the hydraulic system with a liquid supplied via one of the flow paths. A method for operating the extracorporeal blood treatment device is also provided. The hydraulic system has a valve device that provides several switching positions. The valve device has an inlet for a liquid for disinfecting the hydraulic system, and a plurality of outlets. In a first switching position, the inlet is connected to one of the outlets. In another switching position, the inlet is connected to a plurality of the outlets. The inlet of the valve device is in fluid communication with a first flow path and the outlets
(Continued)

are in fluid communication with another flow path. Disinfecting liquid can simultaneously be supplied to the individual flow paths.

13 Claims, 4 Drawing Sheets

(52) U.S. Cl.
CPC ....... *A61M 39/223* (2013.01); *A61M 2205/33* (2013.01); *A61M 2205/75* (2013.01)

(56) References Cited

U.S. PATENT DOCUMENTS

| | | | |
|---|---|---|---|
| 5,948,247 | A | 9/1999 | Gillerfalk et al. |
| 6,153,102 | A | 11/2000 | Kenley et al. |
| 6,607,697 | B1 | 8/2003 | Muller |
| 2012/0308431 | A1 | 12/2012 | Kotsos et al. |

FOREIGN PATENT DOCUMENTS

| | | | |
|---|---|---|---|
| JP | 2001112863 | A | 4/2001 |
| JP | 2003310749 | A | 11/2003 |
| JP | 2004313522 | A | 11/2004 |
| JP | 2015159994 | A | 9/2015 |

OTHER PUBLICATIONS

International Preliminary Report on Patentability issued in corresponding International Patent Application No. PCT/EP2018/054197 dated Aug. 27, 2019 (with English translation) (8 pages).

Office Action issued in corresponding Japanese Patent Application 2019-545931 dated Feb. 10, 2022 (English translation only) (10 pages).

I
II
1
2
2A
2AA
2B
2BA
3
4
5
6
7
8
8A
8B
9
10
11
12
13
14
14A
14A'
14AA
14B
15
15A
15B
16
16A
16B
17
17A
17B
18
19
20
20A
22
23
25A
27A
28A
34
36
37
40
41
42
43
44
45

EXTRACORPOREAL BLOOD TREATMENT DEVICE AND METHOD FOR OPERATING AN EXTRACORPOREAL BLOOD TREATMENT DEVICE

CROSS-REFERENCE TO RELATED APPLICATIONS

This application is a divisional application of U.S. patent application Ser. No. 16/487,103, filed Aug. 20, 2019, which in-turn is a 371 National Phase filing from International Patent Application No. PCT/EP2018/054197, which in-turn claims priority to German Patent Application No. DE 10 2017 001 7790.0, all of which are incorporated herein by reference in their entireties.

FIELD OF THE INVENTION

The invention relates to an extracorporeal blood treatment device having a hydraulic system comprising a plurality of flow paths, the blood treatment device having a control unit which provides an operating mode for disinfecting the hydraulic system with a liquid that can be supplied via one of the flow paths. Moreover, the invention relates to a method for operating an extracorporeal blood treatment device with a hydraulic system comprising a plurality of flow paths.

BACKGROUND OF THE INVENTION

During dialysis, the blood to be treated flows in an extracorporeal blood circuit through the blood chamber of a dialyzer divided by a semi-permeable membrane into the blood chamber and a dialysate chamber, while dialysate flows through the dialysate chamber of the dialyzer. The extracorporeal blood circuit comprises a blood supply conduit, which leads to the blood chamber, and a blood discharge conduit, which leads away from the blood chamber. The hydraulic system of the extracorporeal blood treatment device comprises a plurality of assemblies for the preparation and balancing of the dialysate, which in turn may have several components. The individual components of the hydraulic system are in fluid communication via a plurality of flow paths. The individual flow paths can have one or more conduits. The dialyzer, for example, is supplied with fresh dialysate via a dialysate supply conduit and used dialysate is removed via a dialysate discharge conduit of the dialyzer. Pumps are provided for conveying the liquids. The individual components of the blood treatment device are controlled by means of a control unit.

The dialysate can be produced in the dialysis machine from permeate (pure water) and one or more concentrates. The dialysis machines have a water connection for supplying the permeate.

For the disinfection of the hydraulic system of the blood treatment devices, hot disinfection becomes more important in order to reduce the use of chemicals. In hot disinfection, pure water (permeate) heated to a temperature greater than 80° C. is supplied to the hydraulic system. During the hot disinfection, the heated permeate circulates in the flow paths of the hydraulic system. For a sufficient disinfection, it is crucial that the temperature of the permeate in all flow paths of the hydraulic system does not fall below the predetermined temperature of the permeate.

Blood treatment devices with a device for hot disinfection are known from U.S. Pat. No. 6,153,102 and EP 0 208 090 A1.

The heated permeate is supplied via one of the flow paths of the hydraulic system. Then the permeate spreads in the other flow paths. In practice, it has been shown that in a central supply of the heated permeate via one of the flow paths, the permeate in individual flow paths, which are farther away from the central supply, is cooled down to a temperature which is below the temperature which the permeate has in individual flow paths, which are not as far away from the central supply. Indeed, the cooling down of the disinfecting liquid can be compensated by longer disinfection times or the addition of chemicals. However, longer disinfection times lead to higher energy consumption and the addition of chemicals leads to a higher consumption of chemicals.

SUMMARY OF THE INVENTION

The invention has for its object to provide an extracorporeal blood treatment device which does not give rise to the risk that the temperature required for hot disinfection is not reached when hot disinfection is carried out even if disinfection times are shortened and/or no or only few chemicals are added.

In addition, the invention has for its object to provide a method for operating an extracorporeal blood treatment device that allows for a hot disinfection without the risk of falling below the temperature required for hot disinfection even with shorter disinfection times and/or little or no addition of chemicals.

Another object of the invention is to shorten the disinfection times and/or to reduce the energy consumption and/or the consumption of chemicals.

These objects are achieved according to the invention by the features of the independent claims. The dependent claims relate to advantageous embodiments of the invention.

The blood treatment device according to the invention is characterized in that the hydraulic system has a valve device providing several switching positions. The valve device has an inlet for the liquid for disinfecting the hydraulic system and a plurality of outlets. In a switching position, the inlet is connected to a plurality of outlets. In another switching position, the inlet may not be connected to any of the outlets or to one of the outlets.

In this context, a plurality of outlets is understood to mean a plurality of outlets, which comprises at least two outlets. For example, the valve device may be formed as a multi-way valve having an inlet and two or three outlets. The valve device can also comprise more than one inlet if the valve device is to be supplied with liquid via a plurality of conduits. The hydraulic system may also include a plurality of valve devices.

The inlet of the valve device is in fluid communication with the flow path through which liquid for disinfecting the hydraulic system can be supplied, and the outlets of the valve device are each in fluid communication with another flow path of the hydraulic system, so that in the switching position in which the inlet with multiple outlets is connected, liquid is simultaneously supplied to the individual flow paths. For example, bypass conduits may lead to other flow paths from the outlets of the valve device.

The simultaneous supply of the liquid at different points of the hydraulic system leads to shorter distances. Longer distances, on which the liquid could cool down, are thus avoided. Consequently, it is ensured that the liquid in all the flow paths has the temperature required for the hot disinfection. A valve device having two outlets allows for the simultaneous supply of two flow paths with hot liquid. For example, if the valve device has three outlets, hot liquid can simultaneously be supplied to three flow paths.

The valve device, with which the liquid flow can be controlled in several flow paths, i.e. that can be enabled or disabled, allows a hot disinfection even in those flow paths of the hydraulic system, which could otherwise be hardly supplied with hot liquid or could possibly not be supplied with hot liquid at all.

A preferred embodiment provides that the hot disinfection blood treatment device has a hot disinfection device with a heating unit for heating a liquid, so that the heated liquid can be provided in the blood treatment device. The flow path, via which the liquid for disinfecting the hydraulic system can be supplied, is then in fluid communication with the hot disinfection device. For the supply of a liquid, in particular a permeate, the blood treatment device preferably has a connection with which the flow path, via which the liquid for disinfecting the hydraulic system can be supplied, is in fluid communication. The flow path for the supply of the liquid may thus comprise the conduits leading away from a water connection via the hot disinfection device to the valve device. The valve device is preferably arranged in the hydraulic system in close spatial proximity to the hot disinfection device, so that the conduit sections can be kept short. The liquid used for hot disinfection can also be used to prepare the dialysis liquid.

A further preferred embodiment provides that the hydraulic system has a dialysate supply conduit leading to a dialyzer and a dialysate discharge conduit leading away from the dialyzer, the inlet of the valve device being in fluid communication with the dialysate supply conduit leading to the dialyzer. This fluid communication can be made by switching the valve device inside the dialysate supply conduit or by connecting the inlet of the valve device to a conduit which branches off from the dialysate supply conduit.

The dialyzer preferably has an inlet for supplying dialysate and an outlet for discharging dialysate, wherein the dialysate supply conduit has a connector for connecting to the inlet of the dialyzer and the dialysate discharge conduit has a connector for connecting to the outlet of the dialyzer, so that the dialyzer is separable from the hydraulic system for carrying out the disinfection. The dialysate supply conduit thus ends at the inlet-side connector.

A particularly preferred embodiment provides that the hydraulic system has a dialysate supply conduit leading to a dialyzer and a dialysate discharge conduit leading away from the dialyzer, one of the outlets of the valve device being connected to the dialysate supply conduit via a bypass conduit. In practice, it has been found that the liquid used for the hot disinfection in the dialysate supply conduit has cooled down relatively strongly due to the relatively large conduit lengths. However, this is effectively prevented by directly supplying hot liquid into the dialysate supply conduit via the bypass conduit. The dialyzer is separated from the dialysate supply conduit and the dialysate discharge conduit during hot disinfection, and the supply and discharge conduits are connected to each other via, for example, a bypass conduit or other connection piece. The direct supply of hot liquid into the dialysate supply conduit can take place, for example, at a point downstream of a filter switched inside the dialysate supply conduit to increase the degree of purity of the dialysate.

If the hydraulic system has one or more filters for increasing the degree of purity of the dialysate, which may each be arranged inside one of the flow paths of the hydraulic system, one of the outlets of the valve device may be connected via a bypass conduit to a flow path inside which the filter for increasing the degree of purity of the dialysate is arranged and/or which is in fluid communication with the filter, preferably leads to the filter. Consequently, hot liquid can be supplied directly to this part of the hydraulic system.

However, the direct supply of hot liquid to the above parts of the hydraulic system is only to be understood as an example. A direct supply is possible with the valve device to all parts of the hydraulic system, which could otherwise be achieved only poorly and/or where there is a risk that the liquid cools down due to excessive conduit lengths.

In a preferred embodiment, the valve device is designed such that it can be actuated by the control unit. The valve device may be an electromagnetically, pneumatically or hydraulically operable multiway valve. It can also be the case that the multi-way valve can be actuated by hand alone.

The control unit is preferably configured such that in the operating mode for disinfecting the hydraulic system, the valve device is switched to the switching position in which the inlet is connected to a plurality of outlets, so that a plurality of flow paths can be supplied simultaneously with hot liquid.

In addition, the control unit provides an operating mode for performing the blood treatment, wherein the control unit is preferably configured such that in the operating mode for the blood treatment, the valve device is switched to the switching position in which the inlet is not connected to one of the outlets. During the blood treatment, the outlets for the supply of hot liquid to the relevant flow paths of the hydraulic system are then shut off.

A particularly preferred embodiment of the valve device comprises a hollow cylindrical housing body, in which a cylindrical valve body is rotatably arranged, wherein the inlet and the outlets are bores in the housing body and connecting passages are provided in the valve body which connect the inlet to the outlets. For rotating the valve body, an electromagnetic, in particular electromotive, or pneumatic actuator is preferably provided. However, the valve device can also have, for example, a slide displaceable in a housing body, wherein the passages are formed in the housing body.

The method according to the invention for operating an extracorporeal blood treatment device with a hydraulic system comprising several flow paths provides that, in an operating mode for hot disinfection of the hydraulic system, a liquid heated to a predetermined temperature, which is provided at a central location, is simultaneously supplied via bypass conduits from the central location to several flow paths. One of the flow paths which is supplied with the liquid heated to a predetermined temperature is preferably a flow path leading to a dialyzer. The flow path can also be a flow path leading to a filter for increasing the degree of purity of the dialysate. To carry out the blood treatment, the liquid flow passing through the bypass conduits can be interrupted.

The invention is described in detail below with reference to the drawings, in which:

DETAILED DESCRIPTION OF THE INVENTION

Figure 1:
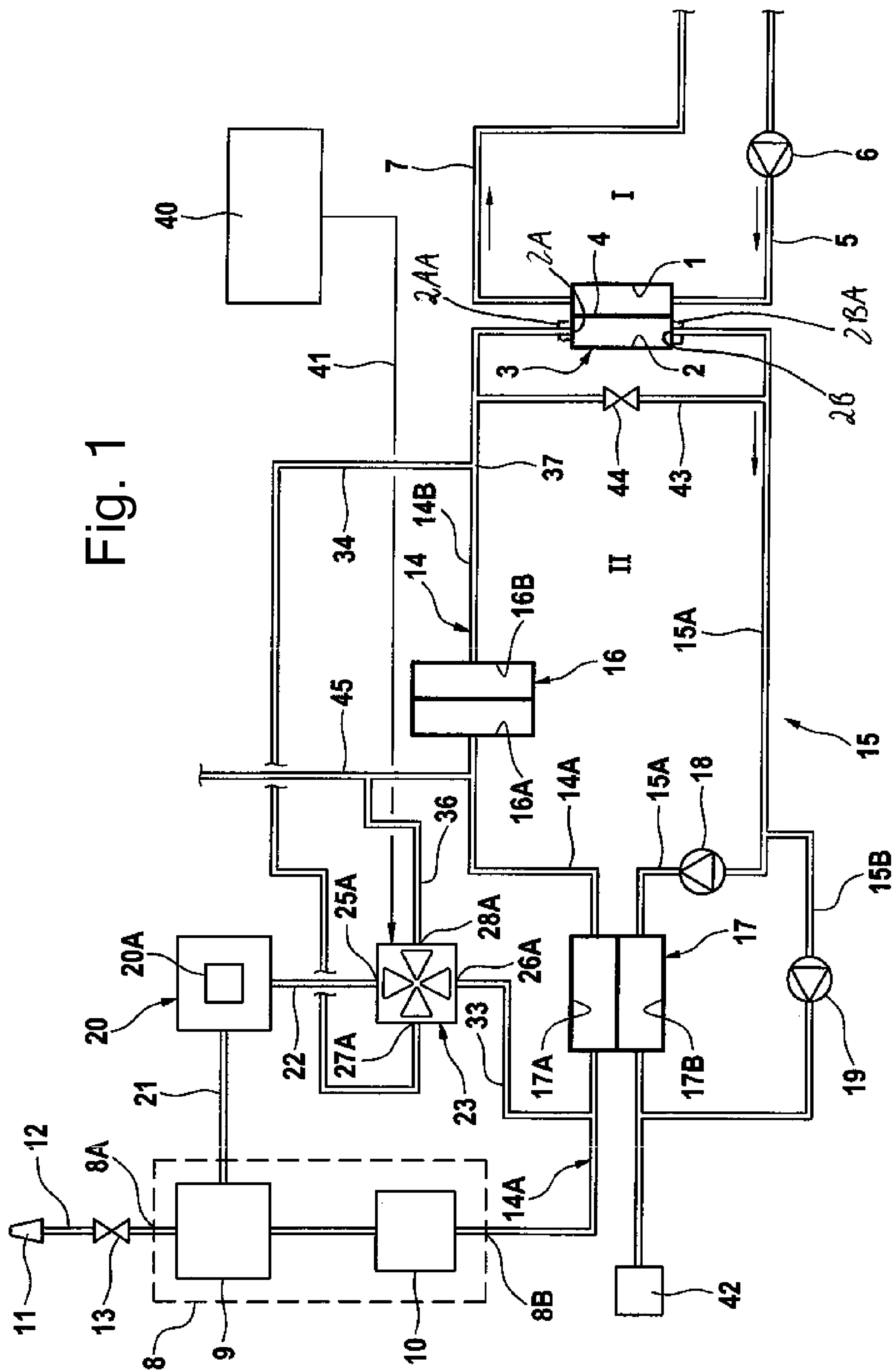
FIG. 1 shows a greatly simplified schematic view of the essential components of one exemplary embodiment of an extracorporeal blood treatment device according to the invention.

First, the essential components of an extracorporeal blood treatment device will be described.

The blood treatment device comprises an extracorporeal blood circuit I and a hydraulic system II. The hydraulic system comprises a plurality of flow paths, which in turn may have a plurality of conduits. In the following, only some of the flow paths and/or conduits are described, which are to be understood as examples of the possible flow paths and/or conduits of a blood treatment device.

The extracorporeal blood circulation I includes the blood chamber 1 and the hydraulic system II includes the dialysate chamber 2 of a dialyzer 3, which is separated by a semi-permeable membrane 4 into the blood chamber 1 and dialysate chamber 2.

To the blood chamber 1 of the dialyzer 3 leads a blood supply conduit 5, inside which a blood pump 6 is switched, while a blood discharge conduit 7 leads away from the blood chamber 1. Together with the blood chamber 1, the blood supply conduit and the blood discharge conduit 5, 7 form the extracorporeal blood circuit I of the blood treatment device.

In order to prepare the dialysate, the hydraulic system B has a dialysate-preparation device 8, that has an inlet 8A for a liquid for producing the dialysate, in particular permeate (pure water), and an outlet 8B. The permeate is collected in an inlet chamber 9. The permeate is mixed with one or more concentrates in a mixing device 10 in order to produce the dialysate.

The permeate is supplied to the blood treatment device at a central connection 11 that is connected to the inlet of the inlet chamber 9 of the dialysate-preparation device 8 via a supply conduit 12. In the supply conduit 12, an inlet valve 13 is provided, so that the hydraulic system II can be separated.

A dialysate supply conduit 14 leads away from the outlet 8B of the dialysate-preparation device 8 to the inlet 2A of the dialysate chamber 2 of the dialyzer 3. For connection to the inlet 2A of the dialyzer 3, the dialysate supply conduit 14 has an only schematically illustrated connector 2AA, with which the dialysate supply conduit 14 can be connected to the inlet of the dialyzer 3. The outlet 2B of the dialysate chamber 2 is connected via a dialysate discharge conduit 15 to a drain 42 for used dialysate. For connecting to the outlet 2B of the dialyzer 3, the dialysate discharge conduit 15 has an only schematically illustrated connector 2BA, with which the dialysate discharge conduit 15 can be connected to the outlet 2B of the dialyzer 3. The connectors may be so-called Hansen clutches.

The dialysate supply conduit 14 has a first section 14A, which leads away from the dialysate processing device 8 to the first chamber 16A of a first sterile filter 16. Inside the first section 14A of the dialysate supply conduit 14, the one chamber 17A of a balancing device 17 is switched. From the second chamber 16B of the first sterile filter 16 the second section 14B of the dialysate supply conduit 14 leads away, which leads to the dialysate chamber 3.

The dialysate discharge conduit 15 divides into two sections 15A, 15B leading to the drain 42. Inside the first section 15A, a dialysis liquid pump 18 is switched, while inside the second section 15B an ultrafiltrate pump 19 is switched. In addition, the other chamber 17B of the balancing device 17 is switched inside the first section 15A.

For performing hot disinfection of the hydraulic system II with a liquid heated to a predetermined temperature, which should be above 80° C., the blood treatment device has a hot disinfection device 20, which has a heating unit 20A for heating the liquid to the required temperature. As liquid for the hot disinfection, the liquid is used for the production of the dialysate, in particular permeate. From the inlet chamber 9, a conduit 21 leads to the inlet of the hot disinfection device 20. The outlet of the hot disinfection device 20 is connected via a conduit 22 to the inlet of a valve device 23, which will be described in more detail below.

The dialyzer 3 is separated during the hot disinfection. The second section 14B of the dialysate supply conduit 14 and the first section 15A of the dialysate discharge conduit 15 are connected to each other during the hot disinfection via a bypass conduit 43. On the bypass conduit 43, a bypass valve 44 is provided, which is closed during the blood treatment and opened during hot disinfection.

The conduit 22 leading away from the hot disinfection device 20 to the valve device 23 forms a flow path of the hydraulic system, via which heated liquid is supplied to the hydraulic system during the hot disinfection. Another flow path is formed by the second section 14B of the dialysate supply conduit 14, which leads to the inlet 2A of the dialyzer 3, while the hot disinfection is separated from the dialyzer. This flow path is to be understood as an example of a flow path in which, due to relatively large conduit lengths, the heated liquid may have cooled down below the required minimum temperature. Another example of a flow path is formed by a conduit 45 leading to the sterile filter 16, of which only one conduit section is shown in FIG. 1. This flow path is to be understood as an example of a flow path that is difficult to reach for the heated liquid.

In addition, the blood treatment device for controlling the individual components has a control unit 40. The control unit 40 provides, in addition to the operating mode for performing the blood treatment, an operating mode for performing the hot disinfection. During the hot disinfection, heated dialysate circulates through the conduits or components of the hydraulic system in fluid communication with the conduits.

The blood treatment device may still have other conduits, shut-off devices and other components that are not shown for the sake of clarity.

Figure 2:
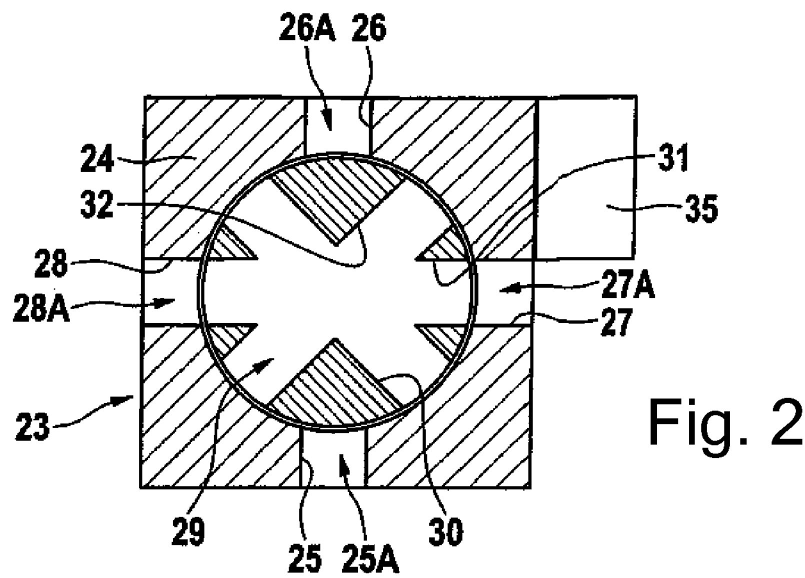
FIG. 2 shows a schematic representation of the valve device in a first switching position.
Figure 3:
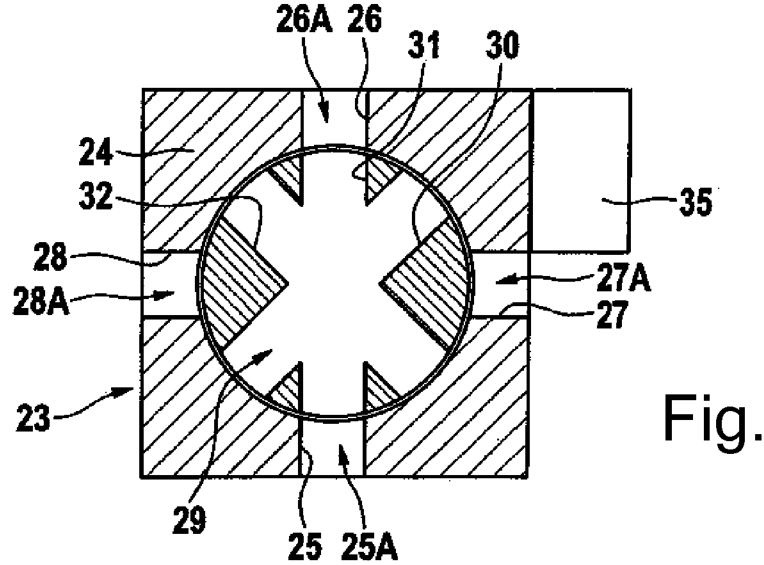
FIG. 3 shows a schematic representation of the valve device in a second switching position.
Figure 4:
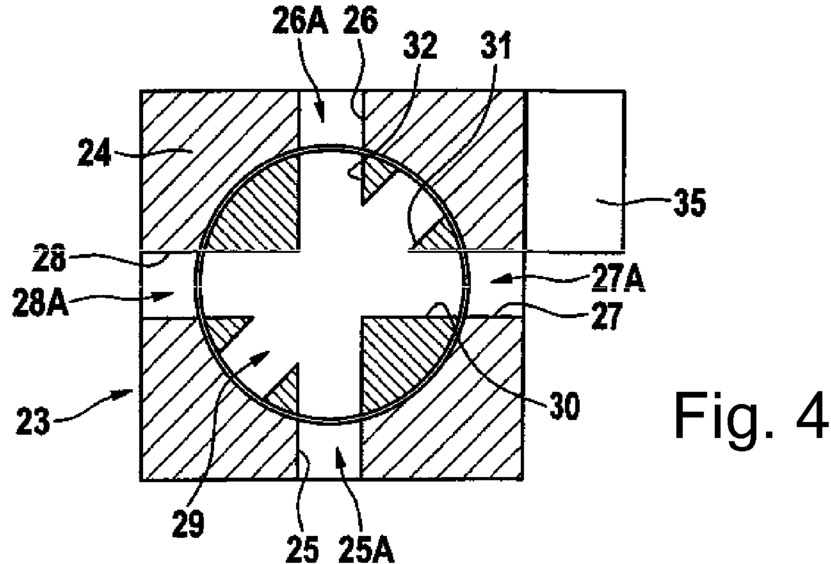
FIG. 4 shows a schematic representation of the valve device in a third switching position.

In FIGS. 2 to 4, the valve device 23 is shown in different switching positions. The valve device 23 has a hollow cylindrical housing body 24, which may be made of plastic or metal. The hollow cylindrical housing body 24 has four bores 25, 26, 27, 28, which extend from the outside into the interior of the housing body 24. In the housing body 24, a cylindrical valve body 29 is rotatably mounted, which may also be made of plastic or metal. The valve body 29 has three passages 30, 31, 32, which intersect in the centre thereof. The passages 30, 31, 32 in the valve body 29 have the same diameter as the bores 25, 26, 27, 28 in the housing body 24. One of the bores 25 forms an inlet 25A and the other bores 26, 27, 28 form outlets 26A, 27A, 28A for the heated liquid. Thus, the valve device has an inlet 25A and three outlets 26A, 27A, 28A.

The bores 25, 26, 27, 28 are on the sides of the housing body 24 and the passages 30, 31, 32 are formed inside the valve body 29 such that the valve device 23 can assume the switching position shown in FIGS. 2 to 5.

The conduit 22 leading away from the hot disinfection device 20 is connected to the inlet 25A of the valve device 23. The first outlet 26A is connected via a conduit 33 to the first conduit section 14A of the dialysate supply conduit 14 upstream of the first chamber 17A of the balancing device 17. The second outlet 27A is connected via a bypass conduit 34 to the second conduit section 14B of the dialysate supply conduit 14 downstream of the sterile filter 16, inside which the risk exists that the heated liquid has cooled down, when it has flowed through the other flow paths. The connection point 37 can be arranged upstream of the connection of the bypass conduit 43 adjacent to the second section 14B of the dialysate supply conduit 14. The third outlet 28A is connected via a bypass conduit 36 to the conduit 45 leading to the sterile filter 16, which is difficult to reach via the other flow paths.

In the first switching position, the inlet 25A of the valve device 23 is closed by the valve body 29. The first outlet 26A facing the inlet 25A is also closed by the valve body 29. On the other hand, the second and third outlets 27A, 28A facing each other on the other sides of the valve body 29 are connected via a passage 31 inside the valve body 29 (FIG. 2).

In the second switching position, the inlet 25A and the inlet-facing first outlet 26A are connected via the passage 31 inside the valve body 29, while the second and third outlet 27A, 28A are closed by the valve body 29 (FIG. 3).

In the third switching position, the inlet 25A and all the outlets 26A, 27A, 28A are interconnected via the passages 30 and 32 inside the valve body 29 so as to divide the flow of liquid flowing through the inlet 25A (FIG. 4).

The valve device 23 has an actuator 35 for adjusting the valve body 29 to the individual switching positions, which is an electric motor actuator in the present embodiment. The actuator 35 is connected to the control unit 40 of the blood treatment device via a control conduit 41. The control unit 40 is configured such that the switching positions shown in the figures can be specified.

In the operating mode for performing the blood treatment, the control unit 40 controls the actuator 35 of the valve device 23 such that the valve device assumes the first switching position in which the inlet 25A is closed, i.e. the inlet is not connected to one of the outlets 26A, 27A, 28A. Consequently, the part of the hydraulic system II intended for hot disinfection is disconnected.

In the operating mode for hot disinfection, the control unit 40 can control the actuator 35 of the valve device 23 such that the valve device assumes the second switching position (FIG. 3) or the third switching position (FIG. 4). The second switching position corresponds to a conventional disinfection operation in which the heated liquid, in particular permeate, is supplied to the hydraulic system II only at one point. The heated permeate flows into the first section 14A of the dialysate supply conduit 14 upstream of the balancing device 17. In the third switching position, the inlet 25A of the valve device is also connected to the two other outlets 27A, 28A, so that heated permeate is simultaneously supplied via the bypass conduits 34, 36 at two further points of the hydraulic system while bypassing difficult to reach or particularly long conduit sections. This ensures that the heated permeate in all conduits of the hydraulic system has the minimum temperature required for hot disinfection.

Figure 5:
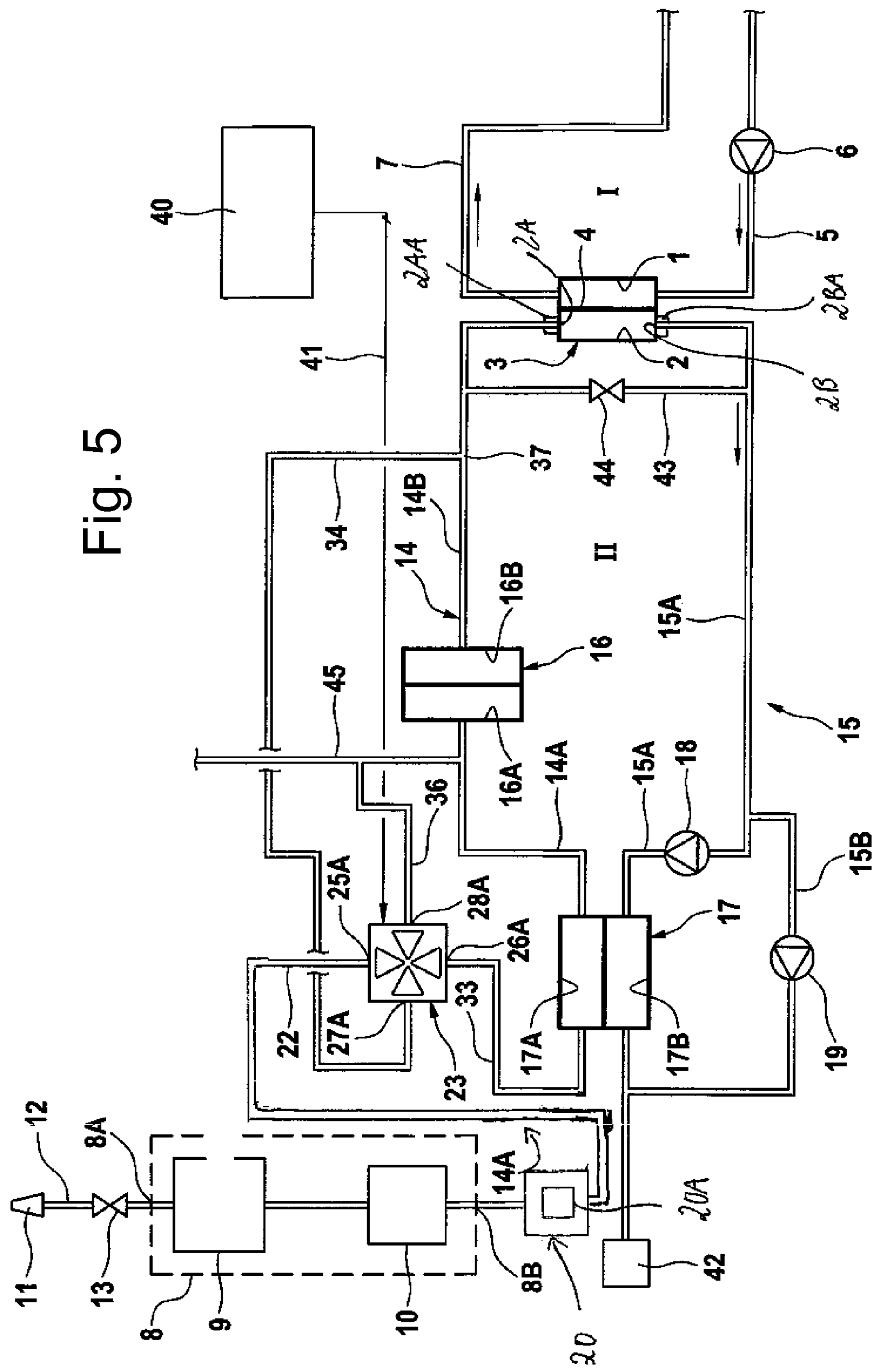
FIG. 5 shows an alternative embodiment of the extracorporeal blood treatment device according to the invention and FIG. 6 shows another alternative embodiment of the extracorporeal blood treatment device according to the invention.

FIG. 5 shows another embodiment of the invention, which differs from the embodiment of FIG. 1 only by the arrangement of the hot disinfection device 20 and the valve device 23. The corresponding parts are provided with the same reference signs.

In the embodiment of FIG. 5, the heating unit 20A of the hot disinfection device 20 is used both for heating the dialysate to the temperature required for blood treatment and for heating the permeate to the temperature required for hot disinfection. In the embodiment of FIG. 5, the valve device 23 is switched inside the dialysate supply conduit 14. The inlet 25A of the valve device 23 is connected to a section of the dialysate supply conduit 14 leading to the valve device 23, while an outlet 26A of the valve device 23 is connected to a section of the dialysate supply conduit 14 that is leading away from the valve device 23. During the blood treatment, in a switching position of the valve device 23, the inlet 25A of the valve device 23 is connected to the outlet 26A of the valve device 23, wherein the inlet 23 is not connected to the other outlets 27A and 28A. For the hot disinfection, the valve device 23 is switched to another switching position, in which the inlet 25A of the valve device 23 is connected to the two outlets 27A and 28A, so that permeate, which is heated to the temperature required for hot disinfection, is simultaneously directly supplied via the two flow paths comprising the conduits 34 and/or 36 to the hydraulic system II. As a result, long flow paths are avoided, so that the permeate cannot cool down. In this switching position, the inlet 25A of the valve device 23 can also be connected to the outlet 26A, so that heated permeate can flow via the conduit 33 into the balancing device 17.

Figure 6:
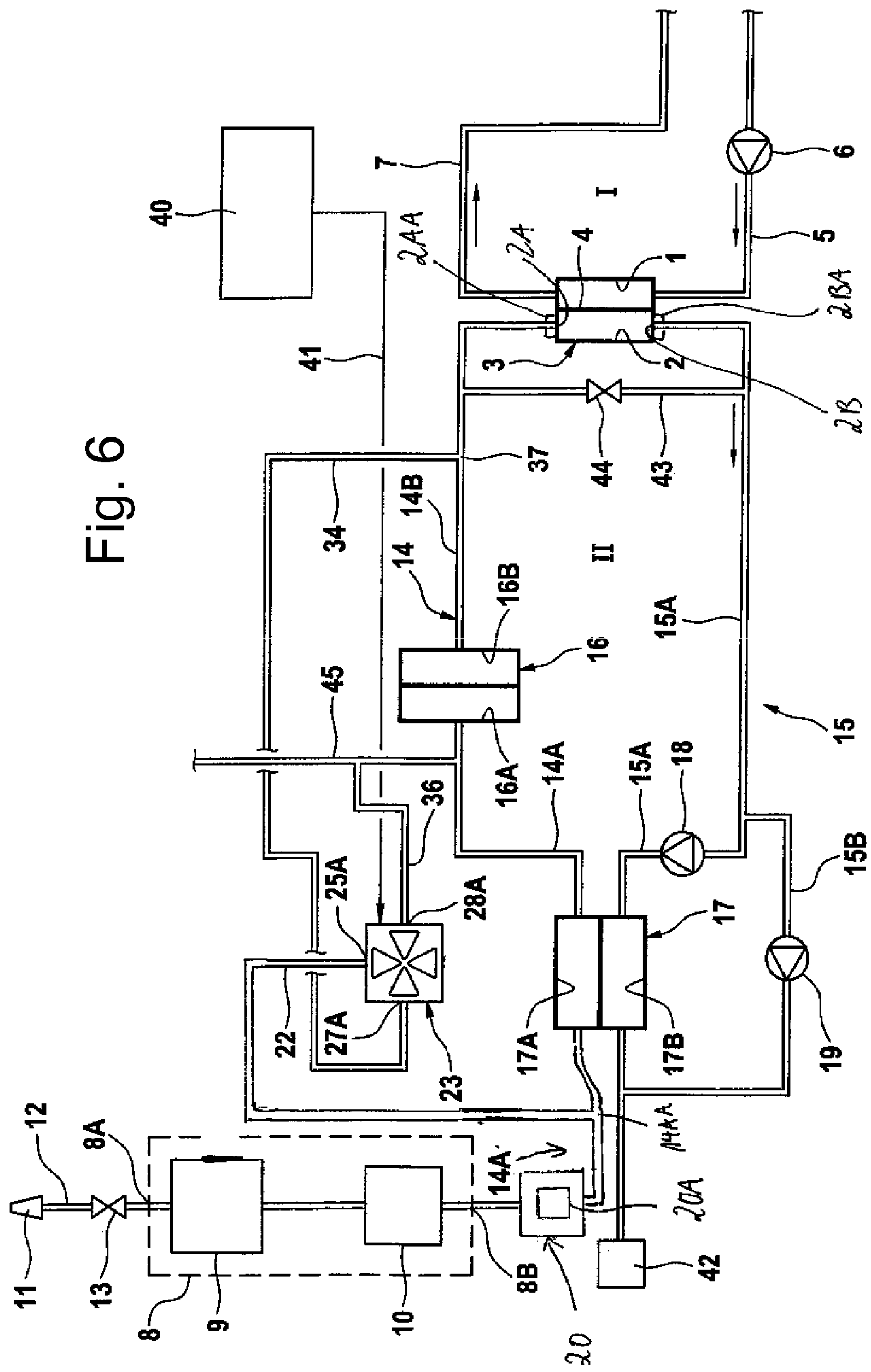

FIG. 6 shows another embodiment of the invention, which differs from the embodiment of FIG. 5 only by the arrangement and design of the valve device 23. The corresponding parts are again provided with the same reference signs. Also in the embodiment of FIG. 6, the heating unit 20A is used both to heat the dialysate for blood treatment and to heat the permeate to a higher temperature for hot disinfection. Other than in the case of FIG. 5, the valve device 23 is not switched inside the dialysate supply conduit 14, but is connected via a conduit 22 to the flow path in fluid communication, via which the liquid for the production of dialysate and/or liquid for the disinfection of the hydraulic system II can be supplied. The conduit 22 connected to the dialysate supply conduit 14 at the junction 14AA connects a section of the dialysate supply conduit 14, preferably a section between the heating unit 20A and the balancing means 17, i.e. a section in close proximity to the heating unit 20A, to the inlet 25A of the valve device 23. In the present embodiment, the valve device 23 has only two outlets 27A and 28A, which are connected to the conduits 34 and 36. However, it is also possible to provide further outlets which lead via further flow paths to different points of the hydraulic system II.

What is claimed is:

1. An extracorporeal blood treatment device comprising a hydraulic system comprising a plurality of flow paths, the blood treatment device comprising a control unit configured to provide an operating mode for disinfecting the hydraulic system with a liquid that is supplied via one of the flow paths of the plurality of flow paths, wherein the hydraulic system comprises a multi-switch valve device having an inlet for the liquid for disinfecting the hydraulic system, and a plurality of outlets, the inlet of the valve device is in fluid communication with a first flow path of the plurality of flow paths, via which liquid for disinfecting the hydraulic system is supplied, and each of the outlets of the plurality of outlets is in fluid communication with a different flow path of the plurality of flow paths, in a switching position of the valve device, the inlet is connected to a plurality of outlets of the plurality of outlets, the hydraulic system has a dialysate supply conduit leading to a dialyzer, and a dialysate discharge conduit leading away from the dialyzer, one of the outlets of the plurality of outlets is connected, via a bypass conduit, to the dialysate supply conduit, the hydraulic system comprises a filter for increasing the degree of purity of the dialysate, which is arranged inside one of the flow paths of the plurality of flow paths, and one of the outlets of the plurality of outlets is connected, via a bypass conduit, to a conduit leading to the filter.

2. The extracorporeal blood treatment device according to claim 1, wherein, in a switching position of the valve device, the inlet is connected to none of the outlets of the plurality of outlets.

3. The extracorporeal blood treatment device according to claim 1, wherein, in a switching position of the valve device, the inlet is connected to one of the outlets of the plurality of outlets.

4. The extracorporeal blood treatment device according to claim 1, wherein the blood treatment device comprises a hot disinfection device having a heating unit for heating a liquid for hot disinfection, and the flow path through which the liquid for disinfecting the hydraulic system can be supplied is in fluid communication with the hot disinfection device.

5. The extracorporeal blood treatment device according to claim 1, wherein the blood treatment device has a connection for a supply of a liquid, and the connection is in fluid communication with the flow path via which the liquid for disinfecting the hydraulic system is supplied.

6. The extracorporeal blood treatment device according to claim 1, wherein the inlet of the valve device is in fluid communication with the dialysate supply conduit leading to the dialyzer.

7. The extracorporeal blood treatment device according to claim 6, wherein the dialyzer has an inlet for supplying dialysate and an outlet for discharging dialysate, the dialysate supply conduit has a connector for connecting to the inlet of the dialyzer, the dialysate discharge conduit has a connector for connecting to the outlet of the dialyzer, and the dialyzer is separable from the hydraulic system, for disinfection.

8. The extracorporeal blood treatment device according to claim 7, wherein the valve arrangement is switched inside the dialysate supply conduit.

9. The extracorporeal blood treatment device according to claim 1, wherein the valve device is designed such that the valve device can be actuated by the control unit.

10. The extracorporeal blood treatment device according to claim 1, wherein the control unit is configured such that, in the operating mode for disinfecting the hydraulic system, the valve device is switched to a switching position in which the inlet is connected to a plurality of the outlets of the plurality of outlets.

11. The extracorporeal blood treatment device according to claim 1, wherein the control unit provides an operating mode for performing blood treatment, and the control unit is configured such that, in the operating mode for performing blood treatment, the valve device is switched to a switching position in which the inlet is not connected to any of the outlets of the plurality of outlets.

12. The extracorporeal blood treatment device according to claim 1, wherein the valve device comprises a hollow cylindrical housing body in which a cylindrical valve body is rotatably arranged, the inlet, and the plurality of outlets, are bores in the hollow cylindrical housing body, and passages connecting the inlet to the plurality of outlets are provided in the cylindrical valve body.

13. The extracorporeal blood treatment device according to claim 12, wherein, for rotating the cylindrical valve body, an electromagnetic, electromotive, or pneumatic actuator is provided.

* * * * *